United States Patent [19]

Kleschick

[11] Patent Number: 4,532,328

[45] Date of Patent: Jul. 30, 1985

[54] PROCESS FOR MAKING OPTICALLY ACTIVE ESTERS OF PHENOXYPHENOXYPROPIONIC ACIDS OR PYRIDYLOXYPHENOXYPROPIONIC ACIDS

[75] Inventor: William A. Kleschick, Concord, Calif.

[73] Assignee: The Dow Chemical Company, Midland, Mich.

[21] Appl. No.: 513,575

[22] Filed: Jul. 14, 1983

[51] Int. Cl.³ .................... C07D 213/64; C07C 69/88
[52] U.S. Cl. .................................... 546/302; 560/62; 560/61
[58] Field of Search .................... 560/62, 61; 546/302

[56] References Cited

FOREIGN PATENT DOCUMENTS 0002800 12/1978 European Pat. Off. ............ 546/302
0003890 9/1979 European Pat. Off. ............ 546/302

*Primary Examiner*—Alan L. Rotman

[57] ABSTRACT

Process for making optically active esters having an enhanced optical purity by reacting a mole of an appropriate substrate phenol with a molar excess of an appropriate optically active ester.

6 Claims, No Drawings

PROCESS FOR MAKING OPTICALLY ACTIVE ESTERS OF PHENOXYPHENOXYPROPIONIC ACIDS OR PYRIDYLOXYPHENOXYPROPIONIC ACIDS

BACKGROUND OF THE INVENTION

The herbicidal activity of a great number of derivatives of variously substituted pyridyloxyphenoxypropionic acids is well known in the art, see for example, European Patent No. 483. The variations in herbicidal effectiveness of the optically active isomers of these compounds is also known, the R isomer being the most active herbicide, and this is taught, for example, in European Patent Application Nos. 2800, 3890 and 6608, German OLS No. 29 49 728 and British Pat. No. 2,042,503.

DESCRIPTION OF THE PRIOR ART

Various methods for obtaining high concentrations of the R-isomer are known. For example, European Patent Application No. 3890 teaches the reaction of one equivalent of the S-form of alpha-bromo propionic acid with one equivalent of the desired pyridyloxphenol to prepare the R-form of the pyridyloxyphenoxypropionic acid, the purity of the final product being largely determined by the purity of the starting propionic acid. Theoretically by this method one can obtain essentially pure product, i.e., one containing essentially 100% of the R-form. In practice, however, the prior art methods generally provide products containing from 70 to 90% of the R-isomer and, correspondingly, 10 to 30% of the S-isomer. Such products are said to have an optical purity of 40 to 80%, i.e., from 40 to 80% of the mixture is the R-isomer and 60 to 20% is a racemic mixture.

SUMMARY OF THE INVENTION

This invention provides a process for making optically active esters of compounds having the formula

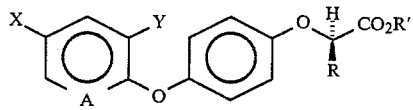

wherein X is $CF_3$, $CF_2Z$, H, Cl or F; Y is H, Cl or F; Z is H or Cl; A is N or —CH; and R and R' are independently lower alkyl and wherein the optical purity is enhanced comprises reacting one mole of a phenol compound having the formula

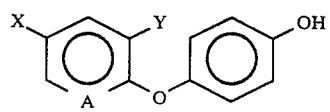

with an excess of an optically active alkanoate ester substituted in the 2-position with a leaving group and having the formula

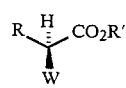

wherein W is halogen, alkylsulfonate or arylsulfonate in a dry inert solvent. This excess can be anywhere from a slight excess to a one hundred fold excess. Typically, excesses in the range of five to twenty-fold are used. The excess reagent may be recovered during a purification step. The reaction can be carried out in a range of dry inert solvents. Typically, polar aprotic solvents such as dimethylsulfoxide (DMSO) or dimethylformamide (DMF) are used. The reaction may be carried out at temperatures from ambient temperature to 100° C.

DETAILED DESCRIPTION OF THE INVENTION

The term "lower alkyl" as used herein refers to alkyl groups which may be straight or branched chain and which contain from 1 to 8 carbon atoms, preferably 1 to 4 carbon atoms.

The alkanoate ester is most preferably employed in an amount of about 10 moles per mole of phenol compound.

The invention is further illustrated by the following examples.

EXAMPLE 1

Preparation of the R-isomer of

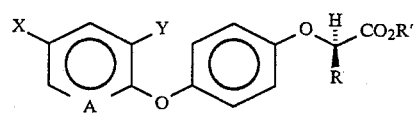

A mixture of 1.92 g (7.50 mmol) of 4-(3,5-dichloro-2-pyridyloxy)phenol, 13.7 g (75.0 mmol) of the methane sulfonate derived from the methyl ester of L-(+)-lactic acid and 1.04 g (7.50 mmol) of anhydrous $K_2CO_3$ in 16 ml of dry DMSO was stirred at room temperature for 42 hours. The reaction mixture was partitioned between $Et_2O$ and $H_2O$ and the organic phase was separated and dried ($Na_2SO_4$). Evaporation gave a pale yellow liquid which was chromatographed on silica gel eluting with EtOHe-hexane (1:9, v/v) to afford 1.90 g (74%) of the desired product as a colorless oil, $[\alpha]_D^{25} +27.1°$ (CHCl$_3$, C 0.0122 g/ml):IR (CCl$_4$) 1767 and 1742 cm$^{-1}$; $^1$H NMR (CDCl$_3$) δ 7.91 (1H, d), 7.70 (1H, d), 6.7–7.2 (4H, m), 4.71 (1H, q), 3.73 (3H, s) and 1.59 (3H, d).

Analysis: Calc'd. for $C_{15}H_{13}Cl_2NO_4$: C, 52.65; H, 3.83; N, 4.09. Found: C, 52.55; H, 3.77; N, 3.97.

The optical purity of the product was determined to be 66% ee (83% R, 17% S) by examination of the $^1$H NMR spectrum in the presence of Eu(tfc)$_3$.

EXAMPLE 2

Preparation of the R-isomer of

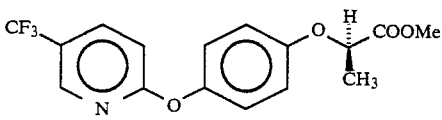

A mixture of 1.91 g (7.50 mmol) of 4-(5-trifluoromethyl-2-pyridyloxy)phenol, 13.7 g (75.0 mmol) of the methanesulfonate derived from the methyl ester of L-(+)-lactic acid and 1.04 g (7.50 mmol) of anhydrous $K_2CO_3$ in 16 ml of dry DMSO was stirred at room temperature for 42 hours. The reaction mixture was partitioned between $Et_2O$ and $H_2O$ and the organic phase was separated and dried ($Na_2SO_4$). Evaporation gave a pale yellow liquid which was chromatographed on silica gel eluting with EtOAc-hexane (1:9, v/v) to afford 1.64 g (64%) of the desired product as a colorless oil, [α]$_D^{25}$ +33.0° (CHCl$_3$, C 0.0103 g/ml): IR (CCl$_4$) 1767 and 1742 cm$^{-1}$; $^1$H NMR (CDCl$_3$) δ 8.3–8.5 (1H, m), 7.83 (1H, d of d), 7.7–8.3 (5H, m), 4.72 (1H, q), 3.76 (3H, s) and 1.62 (3H, d); $^{19}$F NMR (CDCl$_3$) 108 ppm upfield from hexafluorobenzene (s).

Analysis: Calc'd. for C$_{16}$H$_{14}$F$_3$NO$_4$: C, 56.31; H, 4.13; N, 4.10. Found: C, 55.96; H, 4.05; N, 3.98.

The optical purity of the product was determined to be 78% ee (89% R, 11% S) by examination of the $^1$H NMR spectrum in the presence of Eu(tfc)$_3$.

EXAMPLE 3

Preparation of mixed isomers of

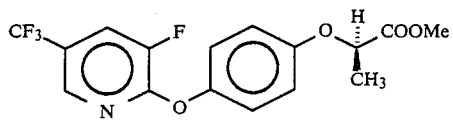

A mixture of 319 mg (1.17 mmol) of 4-(3-fluoro-5-trifluoromethyl-2-pyridyloxy)phenol, 144 mg (1.17 mmol) of (S)-methyl 2-chloropropionate and 162 mg (1.17 mmol) of anhydrous K$_2$CO$_3$ in 2.5 ml of dry DMSO was stirred vigorously at room temperature for 48 hours. The reaction mixture was partitioned between Et$_2$O and H$_2$O, and the organic phase was separated, dried (Na$_2$SO$_4$) and evaporated to yield a nearly colorless oil. The crude product was chromatographed on silica gel eluting with EtOAc-hexane (3:22, v/v) to afford 355 mg (85%) of the desired product as a colorless oil, [α]$_D^{25}$ +10.5° (CHCl$_3$, C 0.0109 g/ml). Examination of the $^1$H NMR spectrum in the presence of Eu(tfc)$_3$ and comparison of the optical rotation with a sample previously prepared using ten equivalents of the methane sulfonate derived from methyl ester of L-(+)lactic acid established the optical purity at 30% ee (65% R and 35% S).

EXAMPLE 4

Preparation of the R-isomer of

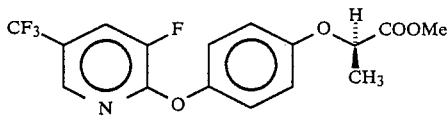

A mixture of 0.5 g (1.8 mmol) of 4-(3-fluoro-5-trifluoromethyl-2-pyridyloxy)phenol, 4.49 g (36.6 mmol) of (S)-methyl 2-chloropropionate and 0.25 g (1.8 mmol) of K$_2$CO$_3$ in 10 ml of dry DMSO was vigorously stirred at room temperature for 16 hours. The reaction mixture was partitioned between Et$_2$O and H$_2$O. The organic phase was separated, dried (Na$_2$SO$_4$) and evaporated to yield the crude product. The crude product was Kugelrohr distilled to yield 0.5 g (76%) of the desired product as a colorless oil, [α]$_D^{25}$ +29.3° (CHCl$_3$, C 0.010 g/ml). The optical purity was 84% ee (92% R and 8% S).

EXAMPLE 5

Preparation of the R-isomer of

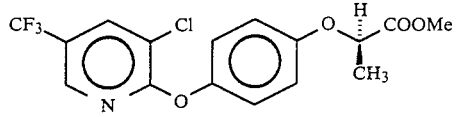

A mixture of 12.8 g (70.0 mmol) of the methane sulfonate derived from the methyl ester of L-(+)-lactic acid, 2.03 g (7.00 mmol) of 4-(3-chloro-5-trifluoromethyl-2-pyridyloxy)phenol and 0.968 g (7.00 mmol) of powdered anhydrous K$_2$CO$_3$ in 14 ml of dry DMSO was stirred at room temperature for 37 hours. The reaction mixture was partitioned between Et$_2$O and H$_2$O. The organic phase was separated and dried (MgSO$_4$). Evaporation gave a nearly colorless oil which was chromatographed on silica gel eluting with EtoAc-hexane (3:22, v/v) to afford 2.05 g (78%) of the desired product as a colorless oil, [α]$_D^{25}$ +31.6° (CHCl$_3$, C 0.0106 g/ml); IR (CCl$_4$) 1767 and 1742 cm$^{-1}$; $^1$H NMR (CDCl$_3$) δ 8.1–8.3 (1H, m), 7.8–8.0 (1H, m), 6.7–7.2 (4H, m), 4.73 (1H, q), 3.76 (3H, s) and 1.61 (3H, d).

Analysis: Calc'd. for C$_{16}$H$_{13}$ClF$_3$NO$_4$: C, 51.15; H, 3.49; N, 3.73. Found: C, 50.95; H, 3.44; N, 3.63.

The optical purity of the product was determined to be greater than or equal to 90% ee (95% R, 5% S) by examination of the $^1$H NMR spectrum in the presence of Eu(tfc)$_3$.

EXAMPLE 6

Preparation of (S)-Methyl Lactate (a) From Ethyl (S)-Lactate by Transesterification. A solution of 11.8 g (0.100 mol) of L-(+)-ethyl lactate and 0.95 g (0.0050 mol) of p-toluenesulfonic acid monohydrate in 405 ml of absolute MeOH was heated at reflux for 25 hours. Sodium bicarbonate (0.43 g) was added to neutralize the p-toluenesulfonic acid and the solvent was removed by distillation at atmospheric pressure. The residue was partitioned between Et$_2$O and saturated NaCl solution. The organic phase was separated and dried (Na$_2$SO$_4$) and the Et$_2$O was removed by distillation at atmospheric pressure. The residue was distilled in vacuo through a 15 cm column packed with glass helices to afford 4.79 g (46%) of the desired product as a colorless liquid, bp 59°–60° C. at 30 mm; [α]$_D^{25}$ −8.763° (neat): IR (CCl$_4$) 3550 and 1741 cm$^{-1}$; $^1$H NMR (CDCl$_3$) δ 4.0–4.5 (1H, m), 3.74 (3H, s), 3.14 (1H, broad d) and 1.39 (3H, d).

Analysis: Calc'd. for C$_4$H$_8$O$_3$: C, 46.15; H, 7.75. Found: C, 45.89; H, 7.38.

(b) From L-(+)-Lactic Acid by Alkylation. A solution of 9.01 g (0.100 mol) of L-(+)-lactic acid in 100 ml of dry DMSO was treated with 6.91 g (0.0500 mol) of powdered anhydrous K$_2$CO$_3$ and the resulting mixture was stirred at room temperature for 1 hour. Methyl iodide (6.23 ml, 14.2 g, 0.100 mol) was added and the resulting mixture was stirred at room temperature for 72 hours. The reaction mixture was partitioned between Et$_2$O and cold H$_2$O. The aqueous phase was washed twice with Et$_2$O and the combined Et$_2$O extracts were dried (Na$_2$SO$_4$). The Et$_2$O was removed by distillation at atmospheric pressure and the residue was distilled in vacuo through a 15 cm column packed with glass helices to afford 2.42 g (23%) of the desired product as a colorless liquid, bp 66°–67° C. at 37 mm; [α]$_D^{25}$ −8.930° (neat).

(c) From L-(+)-Lactic Acid by Acid Catalyzed Esterification. A solution of 198 g (2.20 mol) of L-(+)-lactic acid and 1.8 g (0.018 mol) of concentrated $H_2SO_4$ in 360 ml of MeOH and 115 ml of benzene was heated at reflux for 25 hours. Sodium bicarbonate (1.6 g) was added to neutralize the $H_2SO_4$ and the solvent was removed by distillation at atmospheric pressure. The residue was taken up in $Et_2O$ and dried ($MgSO_4$). The $Et_2O$ was removed by distillation at atmospheric pressure, and the residue was refluxed in benzene with azeotropic removal of $H_2O$. The benzene solution was concentrated, taken up in $Et_2O$ and dried ($MgSO_4$). The solvent was removed by distillation at atmospheric pressure, and the residue was distilled in vacuo through a 10 cm vigreaux column to yield 78.5 g (34%) of the desired product as a colorless liquid, bp 74°–75° C. at 36 mm, $[\alpha]_D^{25} -9.032°$ (neat).

EXAMPLE 7

Preparation of the Methane Sulfonate of Methyl (S)-Lactate

A solution of 116 g (1.11 mol) of the methyl ester of L-(+)-lactic acid and 180 ml (1.29 mol) of dry $Et_3N$ in 2000 ml of $CH_2Cl_2$ was cooled to 5° C., and a solution of 95 ml (140 g; 1.2 mol) of methane sulfonyl chloride in 100 ml of $CH_2Cl_2$ was added dropwise over 1 hour. After the addition was complete the cooling bath was removed, and the reaction mixture was allowed to warm to room temperature and stir for 1.5 hours. The reaction mixture was poured into ice cold $H_2O$. The organic phase was separated, washed with 5% HCl, washed with saturated $NaHCO_3$ and dried ($Na_2SO_4$). The solvent was removed by distillation at atmospheric pressure, and the residue was distilled in vacuo through a 10 cm vigreaux column to afford 193 g (96%) of the desired product as a pale yellow liquid, bp 120°–122° C. at 2 mm; $[\alpha]_D^{25} -55.8°$ (CHCl$_3$, C 0.0102 g/ml); IR (CCl$_4$) 1767, 1367 and 1180 cm$^{-1}$; $^1$H NMR (CDCl$_3$) δ 5.11 (1H, q), 3.80 (3H, s), 3.13 (3H, s) and 1.61 (3H, d).

Analysis: Calc'd. for $C_5H_{10}O_5$: C, 32.96; H, 5.53; N, 17.60. Found: C, 32.55; H, 5.26; N, 17.38.

EXAMPLE 8

A solution of 869 mg (3.00 mmol) of 4-(3-chloro-5-trifluoromethyl-2-pyridyloxy)phenol in 6 ml of dry DMSO was treated with 208 mg (1.50 mmol, of $K_2CO_3$. The resulting red reaction mixture was stirred for 1.5 hours. A solution of 671 mg (3.00 mmol) of crude methane sulfonate of (s) n-butyl lactate in 1.5 ml of dry DMSO was added and the reaction mixture was stirred at room temperature for 24 hours and at 60° C. for 44 hours. The reaction mixture was cooled to room temperature, diluted with $H_2O$ and extracted twice with diethyl ether. The combined ether extracts were washed with $H_2O$ and dried with $Na_2SO_4$. Evaporation gave 1.11 g of amber oil which was chromatographed on silica gel (HPLC) eluting with EtOAc-hexane (2:23, v/v) to afford 0.79 g (63%) of the n-butyl ester of 2-(4-((3-chloro-5-(trifluoromethyl)pyridinyl)oxy)phenoxy)-propionic acid as a colorless oil: $[\alpha]_D^{25} +22.7°$ (acetone, C 0.0102 g/ml); IR (CCl$_4$) 1738 and 1762 cm$^{-1}$; $^1$HNMR (CDCl$_3$) δ 8.1–8.3 (1H, m), 7.8–8.0 (1H, m), 6.7–7.2 (4H, m), 4.71 (1H, q), 4.14 (2H, t), 0.7–1.8 (10H, m including d at 1.61).

Analysis: Calc'd. for $C_{19}H_{19}ClF_3NO_4$: C, 54.62; H, 4.58; N, 3.35. Found: C, 54.52; H, 4.76; N, 3.28.

The $^1$HNMR spectrum of the above n-butyl ester was recorded in the presence of tris[3-(trifluoromethylhydroxymethylene)-d-camphorato], europium (III) derivative. The quartet originally appearing at δ 4.71 was resolved into two quartets in a 4:1 ratio. This observation is indicative of the presence of an 80:20 mixture of the R:S enantiomers of the n-butyl ester (60% ee).

A solution of 26.3 g (0.180 mol) of (s) n-butyl lactate and 28 ml (20 g; 0.20 mol) of dry $Et_3N$ in 420 ml of dry $CH_2Cl_2$ was cooled in an ice bath and 14.3 ml (21.2 g, 0.185 mol) of freshly distilled $CH_3SO_2Cl$ was added over 2 minutes. The ice bath was removed and the reaction mixture was stirred at room temperature for 1 hour. The reaction mixture was partitioned between diethyl ether and cold $H_2O$. The organic phase was washed with 5% HCl, saturated $NaHCO_3$ and saturated NaCl, and dried with $Na_2SO_4$. Evaporation gave the crude methane sulfonate as a pale yellow liquid. A solution of the crude methane sulfonate in 36 ml of dry DMSO was treated with 5.00 g (17.3 mmol) of 4-(3-chloro-5-(trifluoromethyl)pyridinyl)oxyphenol and 2.39 g (17.3 mmol) of anhydrous $K_2CO_3$. The resulting red mixture was stirred at room temperature for 21 hours. The reaction mixture was partitioned between diethylether and $H_2O$. The organic phase was dried with $Na_2SO_4$ and evaporated to give a nearly colorless liquid. Chromatography (HPLC) on silica gel eluting with EtOAc-hexane (1:24, v/v) gave 3.92 g (54%) of the n-butyl ester as a colorless liquid: $[\alpha]_D^{25} +33.8°$ (CHCl$_3$, C 0.0102 g/ml); IR and NMR spectrum were identical to those for a sample of the n-butyl ester prepared as previously described.

Analysis: Calc'd. for $C_{19}H_{19}ClF_3NO_4$: C, 54.62; H, 4.58; N, 3.35. Found: C, 54.82; H, 4.39; N, 3.24.

Comparison of the rotation of this sample of the n-butyl ester ($[\alpha]_D^{25} =33.8°$) with the rotation of the previously prepared sample of n-butyl ester ($[\alpha]_D^{25} +22.7°$) indicated that this sample consisted of a 95:5 mixture of the R:S enantiomers of the n-butyl ester.

Various modifications may be made in the present invention without departing from the spirit or scope thereof and it is understood that I limit myself only as defined in the appended claims.

I claim:

1. A process for making optically active esters of compounds having the formula

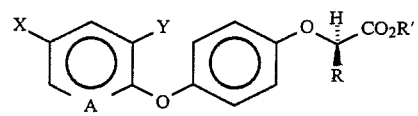

wherein X is $CF_3$, $CF_2Z$, H, Cl or F; Y is H, Cl or F; Z is H or Cl; A is N or —CH; and R and R' are independently lower alkyl and wherein the optical purity is enhanced which comprises reacting one mole of a phenol compound having the formula

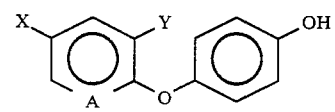

with from 5 to 20 moles of an optically active alkanoate ester substituted in the 2-position with a leaving group and having the formula

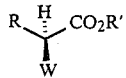
wherein W is halogen, alkylsulfonate or arylsulfonate in a dry inert solvent.
2. Process of claim 1 wherein X is $CF_3$, Y is Cl or F, R is $CH_3$ and R' is a $C_1$ to $C_4$ alkyl group.
3. Process of claim 2 wherein Y is Cl.
4. Process of claim 2 wherein Y is F.
5. Process of claim 3 wherein R' is $CH_3$.
6. Process of claim 4 wherein R' is $CH_3$.
* * * * *